United States Patent [19]
Devlin et al.

[11] Patent Number: 5,981,827
[45] Date of Patent: Nov. 9, 1999

[54] CARBON BASED PROSTHETIC DEVICES

[75] Inventors: David J. Devlin; David W. Carroll, both of Los Almos, N.Mex.; John G. Cowie, Redding, Conn.; Robert S. Barbero, Santa Cruz, N.Mex.

[73] Assignee: Regents of the University of California, Los Alamos, N.Mex.

[21] Appl. No.: 08/967,736

[22] Filed: Nov. 12, 1997

Related U.S. Application Data

[60] Provisional application No. 60/030,861, Nov. 12, 1996.

[51] Int. Cl.$^6$ ............................................ A61F 2/30
[52] U.S. Cl. ............................................ 623/16; 623/18
[58] Field of Search .................................. 623/16, 18

[56] References Cited

U.S. PATENT DOCUMENTS

| | | | |
|---|---|---|---|
| 3,707,006 | 12/1972 | Bokros et al. | 128/92 |
| 4,070,514 | 1/1978 | Eatherly et al. | 428/64 |
| 4,129,470 | 12/1978 | Homsy | 156/155 |
| 4,149,277 | 4/1979 | Bokros | 3/1 |
| 4,166,292 | 9/1979 | Bokros | 3/1 |
| 5,397,365 | 3/1995 | Trentacosta | 623/18 |
| 5,443,513 | 8/1995 | Moumene et al. | 623/16 |
| 5,534,033 | 7/1996 | Simpson | 623/18 |
| 5,645,601 | 7/1997 | Pope et al. | 623/18 |

OTHER PUBLICATIONS

Fitzer et al., Carbon Fibres and Carbon Fibre Reinforced Composites as New Prosthetic Materials, Man–Made Textiles in India, Aug. 1978, pp. 389–395.

E. Fitzer et al., Torsional Strength of Carbon Fibre Reinforced Composites for the Application as Internal Bone Plates, Carbon, 1980, vol.; 18, pp. 383–387.

K. A. Mann et al., Modeling the Tensile Behavior of the Cement–Bone Interface Using Nonlinear Fracture Mechanics, Journal of Biomechanical Engineering, May 1997, vol. 119, pp. 175–178.

J. H. Kuiper et al., Mathematical Optimization of Elastic Properties: Application to Cementless Hip Stem Design, Transactions of the ASME, May 1997, vol. 119, pp. 166–174.

G. M. Jenkins et al., Biomedical Applications of Carbon Fibre Reinforced Carbon in Implanted Prostheses, Carbon, Pergamon Press, 1977, vol. 15, pp. 33–37.

G. M. Jenkins et al., The Fabrication of Artifacts out of Glassy Carbon and Carbon–Fiber–Reinforced Carbon for Biomedical Applications, Journal of Biomedical Materials Research, 1979, vol. 13, pp. 371–394.

P. Christel et al., Development of a Carbon–Carbon Hip Prosthesis, Journal of Biomedical materials Research: Applied Biomaterials, 1987, vol. 21, No. A2, pp. 191–218.

J. C. Bokros, New Material Concepts in Orthopedics, SAMPE Journal, Jul/Aug 1984, pp. 19–22.

*Primary Examiner*—David H. Willse
*Assistant Examiner*—Suzette J. Jackson
*Attorney, Agent, or Firm*—Bruce H. Cottrell

[57] ABSTRACT

A composite article is disclosed including a porous structural member formed of carbon fiber, the porous structural member containing a multiplicity of pores of dimensions greater than about 200 microns in diameter, the porous structural member further including carbon fill material within a portion of the pores such that the pores are essentially less than about 200 microns in diameter, the porous structural member including carbon fill material defining a composite carbon/carbon intermediate article including an outer surface and a thin coating of diamond-like carbon upon the outer surface of the composite carbon/carbon intermediate article. The composite article may serve as a prosthetic device for replacement joints, bone structures and the like.

4 Claims, 2 Drawing Sheets

5,981,827

CARBON BASED PROSTHETIC DEVICES

This application claims the benefit of U.S. Provisional Application No. 60/030,861, filed Nov. 12, 1996.

FIELD OF THE INVENTION

The present invention relates to carbon based prosthetic devices. This invention is the result of a contract with the Department of Energy (Contract No. W-7405-ENG-36).

BACKGROUND OF THE INVENTION

Artificial joints are used to replace joints that are inflicted with diseases or severely injured. These artificial joints are unique mechanical-material systems in that they are exposed to biochemical and dynamic environments of the human body and their design is fixed by anatomy and confined by physiological conditions. Critical design elements in these implants include modulus of elasticity, wear resistance, coefficient of friction, corrosion resistance, and biocompatibility with biological tissue and bone. Within these engineering constraints, prosthetic devices must be designed to remain in the body for a lifetime.

Currently, stainless steel, cobalt-chromium-molybdenum, and titaniumaluminum-vanadium alloys are materials used for the prosthesis stem that anchors into the bone. Bone has a modulus of elasticity ranging from 14 to 28 GPa, whereas, the moduli for these alloys range between 110 GPa to 300 GPa resulting in a difference in the moduli of approximately an order of magnitude. Osteoporosis may result from this large mismatch of elasticity between the bone and the implant due to stress shielding. Such bone transformation and degeneration is one of the factors that can promote stem loosening. Following loosening of the stem, the prosthesis ultimately fractures by a fatigue failure mechanism. Metal prostheses, anchored with methyl methacrylate cement, have a useful life of 7 to 10 years. Bond failure necessitates an entire replacement of the prosthesis. Unfortunately, bone resorption due to the presence of the implant limits the number of implant operations to two per patient. As a consequence, joint replacements are restricted to patients over the age of 55. Thus, the medical profession has a need for improved orthopedic devices and biomaterials. A definite need exists for a new material system for extending the expected life of these prosthetic devices for younger patients. If the prosthetic device could be designed to outlive the patient, young adult patients could receive a device without the need for a second replacement operation or fear of being crippled in their later years of life.

With metal implants low concentrations of metallic ions are released with the possibility of allergic reactions. Also, these materials do not promote bone growth into the implant's surface. Bone ingrowth would provide for superior interfacial strength between the bone and biomaterial that is not observed in existing prosthetic device materials.

The biocompatibility of carbon has been demonstrated and has been permitted in the body for many non-load bearing applications. Heart valves have been produced with isotropic pyrolytic carbon and have been successfully implanted in several hundred thousand patients. Orthopedic pins were coated with diamond-like carbon (DLC) and implanted in laboratory animals. The result of the study was that the DLC coating prevented infection of the tissue attached to the pins. Two dimensional carbon/carbon composites have been used as implants in the femurs of rats. The carbon exhibited excellent biocompatibility with the rough surfaces showing a tendency for bone in growth. Prior test results have indicated that carbon/carbon composites provide improved adaptation to bone over titanium implants. Additionally, carbon fibers have provided a degradable scaffold on which ligaments can be regenerated.

Wear is found on the articulation surfaces of current prostheses. Currently, the femoral heads are generally made from either ceramic or metal alloys. The acetabular cups are composed of ultrahigh molecular weight polyethylene (UHMWPE). Wear of the articulation surfaces has occasionally been found to be so intense that the components have had to be replaced. The average clinical wear factor derived from measurements on 25 replaced prostheses was $2.9 \times 106$ $mm^3/Nm$, with results ranging from $0.09 \times 106$ to $7.2 \times 106$ $mm^3/Nm$. Because penetration rates of the femoral head into the acetabular cup in current forms of total replacement joints are typically in the range of 0.1 to 0.2 mm/year, and overall migrations of the head of 2 or 3 mm is the design limit, the wear lives of implants are in the range of 10 to 30 years. There is increasing concern about the role of wear debris in promoting implant loosening, and consequently there is a need to substantially reduce the volume of wear.

Due to the various limitations of the present implant systems, work has continued on improved implant systems.

One object of the present invention is to produce carbon/carbon composite material with a porosity gradient having about 200 $\mu$m diameter pores in one end and fully densified in the opposite end. The porosity will enhance bone ingrowth, thus providing for high interfacial strength between the stem and bone. The fully dense head will provide a smooth substrate for the surface coating. By varying the porosity of the prosthesis material, and by orienting the carbon fibers optimally, the mechanical properties of an implant may be improved.

Another object of the present invention is to form a diamond like carbon coating onto the fully densified carbon/carbon composite material. An ultra-thin layer of DLC on the carbon/carbon composite (head and acetabular cup) should provide extraordinary wear resistance and low coefficient of friction of the mating surfaces.

Still another object of the present invention is to produce a smooth surface on the head portion of the prosthetic device with such a smooth surface resulting from a porosity of less than 10 $\mu$m, preferably less than about 5 $\mu$m in that portion of the device.

Yet another object of the present invention is to greatly extend the service life of prosthetic devices, e.g., artificial joints, by a materials systems approach employing the union of two or more materials technologies namely the combination of DLC coating technology with carbon/carbon composite material-technology for improved biomedical prostheses. In the case of resultant artificial joints, they should more closely simulate the properties of the actual joint.

SUMMARY OF THE INVENTION

To achieve the foregoing and other objects, and in accordance with the purposes of the present invention, as embodied and broadly described herein, the present invention provides composite article including a porous structural member formed of carbon fiber, said porous structural member containing a multiplicity of pores of dimensions greater than about 200 microns in diameter, said porous structural member further including carbon fill material within a portion of said pores such that the pores are essentially less than about 200 microns in diameter, said porous structural member including carbon fill material defining a composite carbon/carbon intermediate article including an outer surface; and, a thin coating of diamond-like carbon upon said outer surface of said composite carbon/carbon intermediate article.

In one embodiment of the invention, the composite article has a density gradient with a greatest density near the center of said article and a lower density near the surface of said article.

In another embodiment of the invention, the composite article has a gradient density with a greatest density at one end of said article and a decreasing density towards another end of said article.

DETAILED DESCRIPTION

Figure 1:
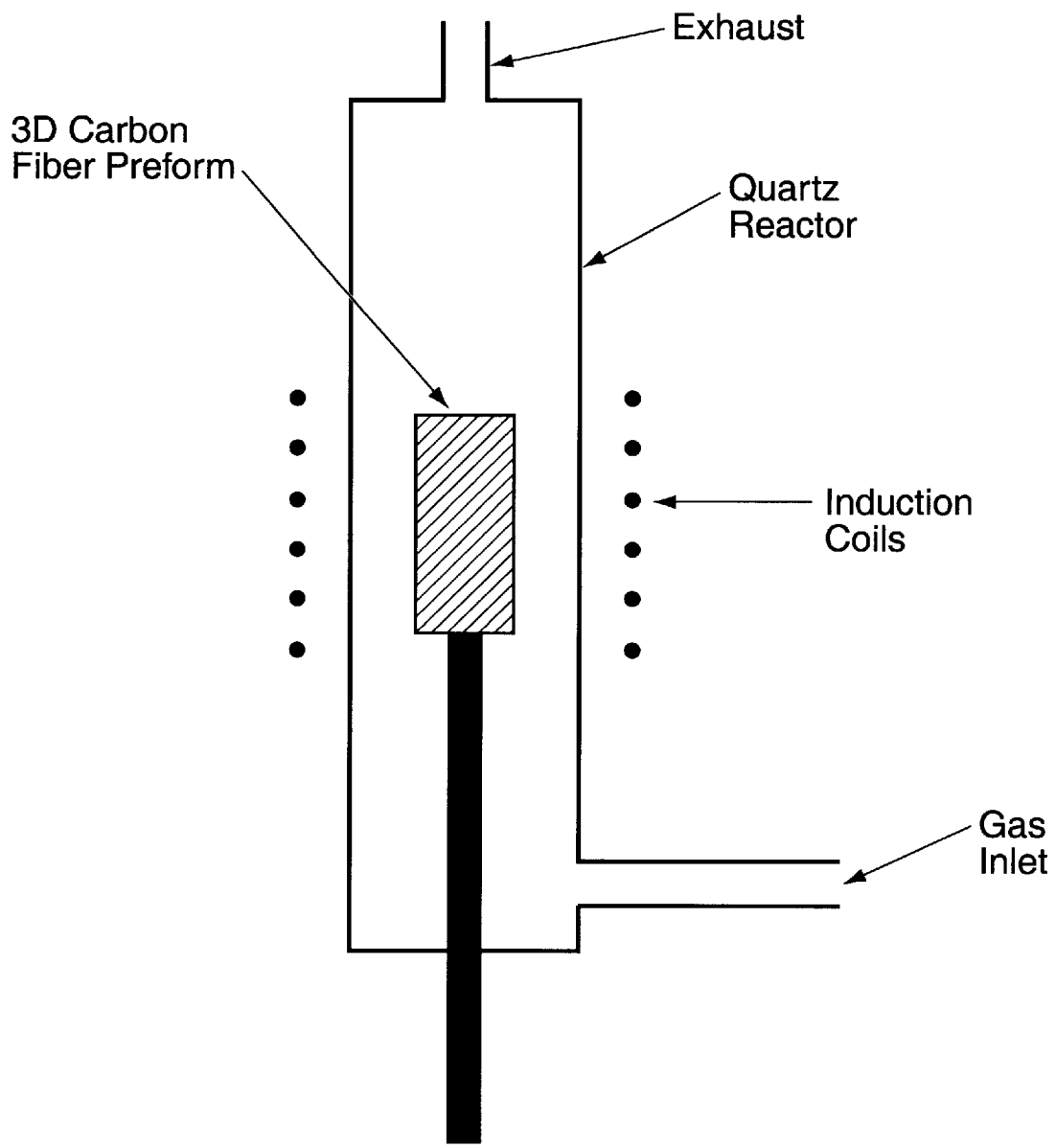
FIG. 1 shows a schematic of a carbon/carbon composite reactor.

The present invention is concerned with carbon based prosthetic devices and to prosthetic devices including a coating of DLC. In contrast to present technology wherein porous coatings are sometimes deposited on metal shafts to promote bone ingrowth, the present system does not suffer from a bonding area that can fail as it (a carbon/carbon composite with a porous gradient) is a single continuous material.

The stresses on the femur in walking have been extensively analyzed. It has been calculated that the maximum tensile or compressive stresses are approximately 48 to 55 MPa. Carbon/carbon composites exhibit tensile strengths of 138 MPa and compressive strengths of 207 to 276 MPa. The femur has a modulus of elasticity ranging from 14 to 28 GPa, compared with 30 to 150 GPa for carbon/carbon composites depending on processing parameters. A femur is composed of various kinds of bone having differing properties and are an isotropic in nature. The ability to tailor the composition of the composite prosthesis by directly controlling the properties in three dimensions is essential in order to replicate the actual bone. Carbon/carbon composites have the potential to satisfy this mechanical property challenge.

In one embodiment of the present invention, the prosthetic device includes a fully dense head portion, i.e., porosity of less than about 50 $\mu$m diameter pores, and includes a stem or shaft portion having a density gradient between the center and the outside or surface. Preferably, the stem of shaft portion is denser at the center with decreasing density near the surface thereby allowing for enhanced bone ingrowth.

Although carbon/carbon composites possess the mechanical and physiological properties essential for use as prostheses, the optimum structure has not been produced. Composites with from about 100 $\mu$m to about 300 $\mu$m diameter pores, suitably around 200 $\mu$m diameter pores, would be very favorable for bone ingrowth. Although carbon/carbon composites exhibit good wear characteristics in certain engineering applications, (e.g., for brakes), the wear rate and resulting debris may not be acceptable for artificial joints without some type of protective surface coating. For fully dense portions of a prosthetic device, the porosity is preferably less than about 50 $\mu$m diameter pores.

Very little work is presented in the open literature concerning the fatigue performance of carbon/carbon. Carbon/carbon composites demonstrate a lifetime of 107 cycles at a stress of 40% of the static bending strength. A Woeler diagram (Stress versus Number of Load Cycles) suggests the material shows a fatigue limit analogous to that of steel. An infinite fatigue life is predicted at 45–50% of the static strength under cyclic loading. Therefore, the fatigue endurance of carbon/carbon appears to be outstanding.

DLC films exhibit extraordinary wear resistance and coefficient of friction, and display exceptional biocompatibility. A thin layer of DLC on a carbon/carbon composite (head and acetabular cup) would provide ideal articulation surfaces for a prosthesis. Such a thin layer is typically from about 1 $\mu$m to about 5 $\mu$m in thickness. While a significant amount of research has been conducted on DLC, there are no reports of coating DLC on carbon/carbon composites. DLC films are characterized by extreme hardness, measured to be in the range 3000 to 9000 kg/mm$^2$. The hardness of DLC is approximately half of that of diamond, and consequently DLC could be expected to exhibit exceptional wear resistance. An interesting feature of DLC is the low coefficient of friction ($\approx$0.14 without any lubrication). DLC has a lower coefficient of friction than the mating components found in present joint prostheses.

DLC coated carbon/carbon composites have numerous potential applications in the medical industry with overall performance applicable to a wide range of biomedical implants not restricted only to artificial joints. The potential service life and compatibility of the DLC coated carbon/carbon composites suggest the potential for application in many joint replacement operations such as hips, knees, shoulders, elbows, and fingers as well as bone replacement operations.

To achieve the objects of the present invention: (1) processing parameters are selected suitable to produce carbon/carbon composites with a gradient of porosity ranging from 200 $\mu$m diameter pores in the stem to a fully densified head; (2) processing parameters are selected suitable to produce carbon/carbon composites with mechanical properties comparable to that of bone; and, (3) processing parameters are selected suitable to coat DLC on the carbon/carbon composites.

Advanced fiber reinforced refractory composites such as carbon/carbon composites offer many advantages over conventional materials. These include high strength at elevated temperatures, low density, corrosion resistance and good wear properties. Carbon/carbon composites have been successfully used in a number of important applications for the past 25 years. Despite the maturity of these markets few advances in processing methods have been made. One of the established methods of carbon/carbon composite manufacturing is chemical vapor infiltration. As is well know, the conventional isothermal process with it's reduced pressures, reactant dilution and low temperatures is time consuming. These conditions are required to insure a uniform infiltration throughout the part. Large kilns with hundreds of parts are typically processed in a batch fashion taking advantage of economy of scale. Long processing times extending to several months are typical. Recent efforts aimed at the development of faster processes have had some success. Methods such as forced flow, thermal gradient, pulsed flow and various combination of these techniques have been explored. Most of these have been applied to ceramic matrix composites. Recently a microwave assisted CVI technique has been reported which takes advantage of the volumetric heating effects that are possible with microwave heating of ceramic materials. Inverted thermal gradients are formed in a preform allowing for rapid CVI processing of 3-D parts. The application of this technique to carbon materials with radio frequency heating is described herein.

A cold wall reactor will minimize unwanted deposition on the walls and fixtures and reduce gas phase nucleation thereby saving on reactant costs, minimizing waste production and allowing for higher pressure processing.

Ordinary radiant heating results in rapid attenuation of the radiation at the surface. Moving down in frequency to the microwave and RF regions of the spectrum the penetration of the radiation into the part increases. The magnetic intensity of the electromagnetic wave decays exponentially with increasing distance into the part. For induction heating the current induced falls off in a similar manner and is characterized as a skin or current depth given by the following relation:

Thus, the degree of volumetric heating depends on the frequency and electrical conductivity of the material. For a carbon fiber preform the electrical conductivity is generally estimated at 25,000 $\Omega^{-1}m^{-1}$. Processing of carbon materials with large bone-like dimensions will require frequencies in the 10 kHz range. As illustrated, the power distribution penetrates the interior resulting in volumetric heating. The temperature distribution falls off at the surface due to radiative and convective losses leading to an inverted temperature gradient. For the deposition of carbon from methane, a difference in temperature of 200° C. can reduce the deposition rate by a factor of 150 near the exterior surface of the pre-form resulting in deposition from the inside-out.

The current depth is another important factor in the establishment of thermal gradients. For a given material this depends on the frequency of radiation and the part dimensions. As the current depth increases relative to the radius of the part, large thermal gradients result. With the proper choice of frequency, and control of the radiative heat loss, thermal gradients can be established.

Composites can be customized through fiber reinforcement to provide strength and stiffness in the required directions. Preferably, the fiber reinforcement can be similar to that of bone where the strength is anisotropic in nature. Satisfactory fatigue strength and fracture toughness, along with the relatively low density of carbon/carbon composites, combine to make the carbon/carbon composite an ideal candidate for prosthetic devices.

Fully dense carbon/carbon composites, by definition, lack the larger (200 $\mu$m) pore size favorable for bone ingrowth into the stem. However, a femoral head requires a fully dense composite for optimum wear characteristics of the articulation surfaces. The first step in developing a new artificial joint is the establishment of suitable processing parameters for producing this carbon/carbon composite with a porosity gradient ranging from 200 $\mu$m diameter pores at one end to fully dense at the other end of the preform. An electromagnetic assisted chemical vapor infiltration (CVI) technique developed at Los Alamos National Laboratory is used for densifying carbon/carbon composites. This process is based on electromagnetic volumetric heating used for rapid densification. The approach utilizes radio frequencies (RF) to achieve the desired inverted temperature gradients in porous carbon/carbon preforms such that densification by CVI can occur from the inside-out as described in a paper by Devlin et al. entitled "Radio Frequency Assisted Chemical Vapor Deposition", in the Proceedings of the Thirteenth International Conference on Chemical Vapor Deposition, vol. 96-5, pp. 571–575, 1996, such description incorporated herein by reference. Volumetric heating, together with heat losses at the surfaces due to radiation and convection, gives rise to "inverted" thermal gradients. With the internal region of the substrate hot, cool reactant gases penetrate inward prior to the onset of the deposition reaction. Consequently, deposition occurs from the inside-out. Inside-out densification minimizes premature pore closure in outer regions, resulting in more spatially uniform composite. Carbon/carbon composites comprised of 3-D continuous fiber reinforcement and a pyrolytic carbon matrix of 2.5 cm diameter have been fabricated to acceptable densities in as little as 30 hours.

Tailoring of the pore size, distribution, and densification gradient from stem to head is desirable. Densification by RF assisted CVI can occur more rapidly at one end of the preform than the other resulting in a porosity gradient with full densification at the hot end. RF frequencies are used to achieve the desired temperature gradients in porous carbon/carbon preforms. The criterion used is the establishment of suitable processing parameters for producing a carbon/carbon composite with a porosity gradient ranging from about 200 $\mu$m diameter pores at one end to a fully dense at the other end of the preform. Densities can generally be within the range of from about 1.4 grams per cubic centimeters (g/cc) to about 1.9 g/cc, preferably about 1.7 g/cc.

Osteoporosis occurs because of stress protection by the prosthetic device mainly due to the mismatch of elasticity between the bone and device. Tailoring of the required elastic and strength properties of prostheses made of carbon fiber reinforced composites may overcome this discrepancy. It has been demonstrated already by medical experiments with animals that the cortical thinning of bones is considerably lessened by the use of carbon fiber reinforced plastic fixation plates with methyl methacrylate as a matrix. As carbon is a material known to be extremely biocompatible, carbon/carbon composite material was also taken into consideration for the use as internal fixation plates. It was demonstrated that the flexural strength and modulus of carbon/carbon bone plates can be well adapted to the mechanical requirements of bone. The strength and modulus of elasticity of the carbon/carbon composite material should closely match the mechanical requirements of the bone it is replacing.

DLC coatings are hydrogenated amorphous carbon films which exhibit high corrosion and erosion resistance, low coefficient of friction, and are perfectly biocompatible. The microstructure of DLC coatings can be controlled by varying deposition variables and substrate variables. The surface morphology and adhesion of this film with the carbon/carbon composite substrate is critical to the performance of the prosthetic device. Plasma assisted chemical vapor deposition (PACVD) techniques have been used routinely for the deposition of DLC. RF plasma deposition methods can be employed for prosthetics coating.

Successful application of DLC onto carbon/carbon composite material requires that the DLC be extremely adherent to the composite material. Additional critical properties of the coating include both high hardness and a smooth surface for high wear resistance. The coefficient of friction must also be as low as possible. Wear rates several orders of magnitude slower than the wear rate for the presently employed metal head on an UHMWPE acetabular cup may be achieved.

With the desired processing parameters for producing a carbon/carbon composite with the required porosity, along with the desired processing parameters for coating hard DLC on the carbon/carbon composite material, the fabrication of a artificial joint may be achieved.

Composites produced for this study have 200 $\mu$m diameter pores which would be very favorable for bone in growth. Although carbon/carbon composites exhibit good wear characteristics in certain engineering applications, the wear rate and potential for resulting debris in artificial joints necessitates a protective surface coating of DLC.

Materials with densities in the range of about 1.7 g/cc are easily fabricated. The matrix shows strong $sp^2$ character as indicated by the Raman spectra. X-ray diffraction results also indicate a strong graphitic nature to the matrix material. Densification by RF assisted CVI can occur more rapidly at one end of the preform than the other resulting in a porosity gradient with full densification at the hot end. The use of RF frequencies to achieve the desired temperature gradients in porous carbon/carbon preforms provided the best results.

RF glow discharges have become an area of intense interest and have been widely utilized in recent years. RF discharge reactors have been used to grow dense carbon films from hydrocarbon gases. The main hydrocarbon source gases have been methane, ethane, butane, propane, acetylene, ethylene, and benzene. Many variables must be controlled in plasma deposition, such as power, total pressure, reactant partial pressures, gas flow rates, pumping speed, sample temperature, discharge frequency, electrode spacing, electrode materials, and reactor geometry.

Generally, the power is controlled at about 50 to 100 Watts, the total pressure is controlled at about $10^{-3}$ mm Hg, the gas flow rate controlled in the range of about 50 to 200 standard cubic centimeter per minute (sccm), the sample temperature is controlled at from about room temperature to about 150° C., the discharge frequency controlled at, e.g., about 13.56 gigahertz (GHz), the electrode spacing is controlled at between about 2 to about 10 cm, the electrode materials are selected from among carbon preforms and stainless steel or the reactor wall, and the reactor geometry can generally be any suitable geometry, e.g., a bell jar.

While the properties of amorphous hydrogenated carbon films may be diamond-like, the structure of this material is far from diamond. Amorphous hydrogenated carbon is a non-crystalline hard network solid with typical hydrogen concentrations around H/C≈0.5 and a mixture of tetrahedral ($sp^3$) and trigonal ($sp^2$) carbon bonding. The hydrogen content critically determines film structure, e.g. the ratio between carbon atoms in different coordinations, and thus the film properties. Useful applications of DLC films are sometimes complicated by adhesion problems and spontaneous buckling, partly due to the large internal compressive stress in the films; however, the incorporation of hydrogen reduces the internal stress of the carbon film.

Processing parameters for successfully applying DLC onto carbon/carbon composite material may be as follows. Generally, the DLC can be applied in a plasma process using a parallel plate process. The deposition system can consist of a diffusion pumped high vacuum chamber with mass flow controllers and conductance values for operation at reduced pressures. The basic process requires the formation of a plasma between a grounded anode and powered cathode. The anode-cathode system is deliberately assymetric such that a negative DC self-bias results at the cathode. The plasma is generated from a hydrocarbon gas such as methane, which is disassociated and ionized in the plasma. Ions are accelerated across the plasma sheath towards the cathode as a result of the self-bias. Ion bombardment is a critical aspect of depositing DLC with the desired properties. For the pressure regime of 6.7 to 13.3 pascals (Pa) biasing on the order of several hundred volts to a thousand volts is required. Low bias potentials result in polymer-like properties while too high of a potential will yield a glassy or graphitic carbon film. Unlike conventional CVD, the ion bombardment aspect of the process results in a line-of-sight deposition. In order to assess the structure of the DLC coating, diagnostic methods have been employed to study the carbon bonding, specifically $sp^3$ and $sp^2$ coordinated carbon atoms. These bonds affect the chemical and mechanical properties of the material. Raman spectroscopy is employed to characterize the DLC coatings produced on the composite to ensure that the desired properties are obtained. The wear resistance and friction coefficients (static and dynamic) of thin DLC films can be measured using a pin-on-disk tribotester.

Figure 2:
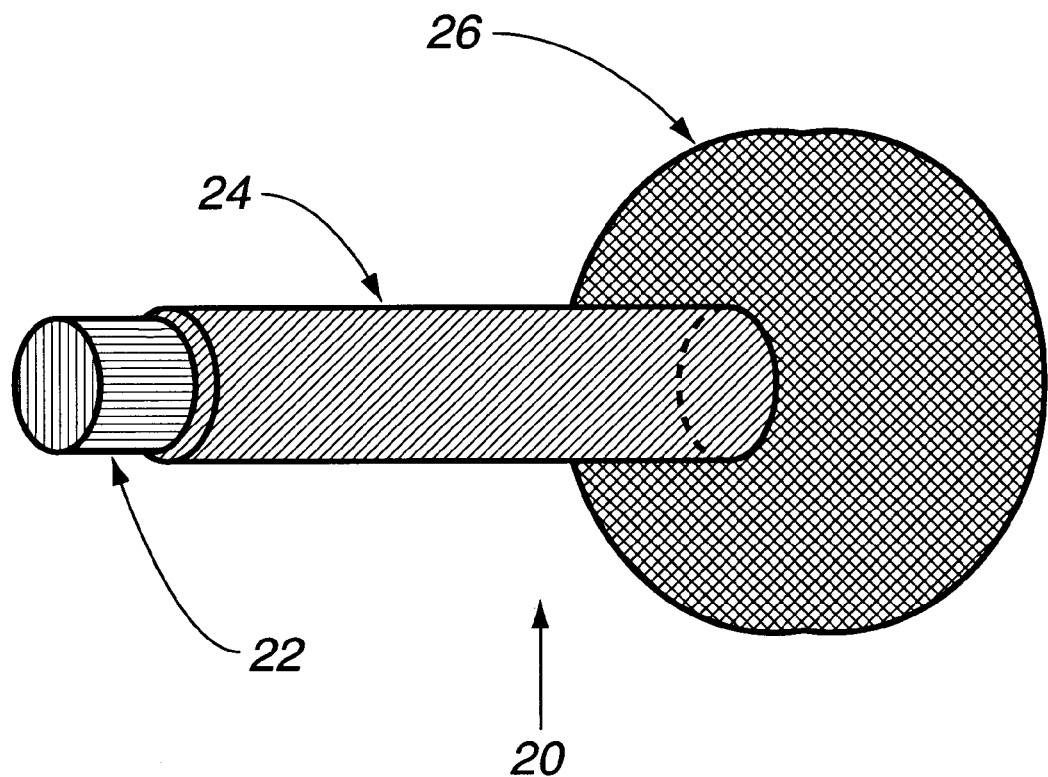
FIG. 2 shows a carbon/carbon composite.

Another system of the present invention involves a stem formed of a unidirectional carbon fiber core with an outer braid sleeve. FIG. 2 illustrates a prosthetic device of such a carbon/carbon composite 20. The unidirectional fiber core 22 provides high strength while the outer carbon fiber braid 24 provides a manner of adjusting the elastic modulus of the material at a bone-device interface and provides a porous surface for bone ingrowth. The head 26 may be 3-D carbon/carbon composite as previously described or can be carbon. Attachment of the head to the stem can be accomplished by chemical vapor infiltration/bonding or by gluing with a suitable adhesive or cement.

In this embodiment, the unidirectional core can be formed from multiple strands of filament carbon fiber tow. For example, about 20 strands of 2000 filament carbon fiber tow yields a total of 40,000 filaments. An outer cylindrical carbon fiber braid having fibers arranged at 45° angles to the alignment of the unidirectional core filaments can be slipped over a bundle of a unidirectional carbon fiber core prior to densification. This preform can then be densified through chemical vapor infiltration by one of two methods.

A first method is the inverted gradient approach where such a preform (about 3 inches in length) is electrically connected at both endes to an AC power supply. A current of 90 amps at 6 volts is continuously passed through the preform resulting in resistive heating of the preform. Preform temperatures can be in the range of about 800° C. to about 1100° C. as measured by an optical pyrometer. Methane (about 200 sccm) at nominal pressures of about 100 Torr can be used to density the preform using infiltration times ranging from about 30 to about 60 hours.

A second method is use of a hot wall furnace. A ten inch length of preform was suspended in a one inch diameter furnace heated to 1100° C. and the furnace was evacuated. Methane (200 sccm) at a nominal pressure of 100 Torr was injected for densification over a period of 30 to 60 hours. This hot wall approach is suitable, as it is not believed necessary to use an inverted gradient approach for this particular fiber architecture in order to produce a graded porosity on the outer surface. The graded porosity will result from the braid structure encasing the unidirectional carbon fiber core.

The present invention is more particularly described in the following example which is intended as illustrative only, since numerous modifications and variations will be apparent to those skilled in the art.

EXAMPLE 1

A reactor consisting of a simple induction coil (as shown in FIG. 1) was operated at 50 kHz. Samples were heated without insulation to temperatures ranging from 1100 to 1400° C. The preforms used were 3D carbon fiber (30 volume percent fiber, obtained from Hitco). These were cut into cylinders approximately 1 inch in diameter by 3 inches in length. The matrix was deposited by pyrolysis of methane at pressures ranging from 100 to 300 torr, with a flow rate of 200 sccm. Temperature gradients were monitored with thermocouples inserted in the preform at various radial positions.

For the process conditions of 1330° C., 100 torr and 200 sccm of methane, the evolution of the temperature gradient from the centerline to the surface was monitored.

An initial increase in ΔT was thought to be caused by preferential deposition on the interior of the preform resulting in stronger coupling of the electromagnetic radiation to the center of the preform. The process was initially self propagating and the total absorbed power required continually decreased. Eventually as deposition near the exterior occurred the temperature gradient decreased. Materials have been processed to densities in the range of 1.7 g/cc in as little as 30 hours. The matrix shows strong $sp^2$ character as indicated by the Raman spectra and X-ray diffraction results.

Experiments were undertaken to evaluate the previously described model for the prediction of temperature gradients. A preform was infiltrated at 1100° C., 300 torr and 200 sccm of methane. Temperatures were monitored at three positions; the center of the preform, approximately halfway from the center to edge, and near the edge. The total power into the part was 6 kW.

To maintain the desired temperature gradients for large dimension parts, a lower frequency may be required. The results of the above experiment allow estimation of the gradients for large parts at different frequencies. Calculations for 10 kHz frequency on a 10 cm diameter cylinder show that the predicted temperature gradients are similar to those calculated and measured for a 1 inch diameter part at 50 kHz.

The approach reduces processing times significantly. For example, typical carbon/carbon processing can run several months. For carbon/carbon materials, RF frequencies are required to heat the part effectively. This type of technology is commonly used in industrial heating. In most large scale processes, like the fabrication of carbon/carbon composites, RF induction heating is used to heat a susceptor which than radiates to the part. Using much of the same processing equipment the part can be heated directly to produce inverted gradients.

EXAMPLE 2

A head was fabricated by inserting a dense stem component into the bottom of a one inch diameter cylindrical 3-D carbon preform. This was densified using the previously described RF process. The result was a dense stem attached by gluing through CVD carbon. Excellent bonding between the head and the stem occurred with a continuous carbon matrix as the bonding agent. In this approach, the outer porosity and dimension of the pores can be adjusted by choice of braid weave parameters. The spacing between fiber tows in the weave and the angle of the weave could be adjusted as necessary. Core strength and stiffness can be adjusted by varying the core fiber volume fraction.

Although the present invention has been described with reference to specific details, it is not intended that such details should be regarded as limitations upon the scope of the invention, except as and to the extent that they are included in any accompanying claims.

What is claimed is:

1. A composite article comprising:
a porous structural member formed of carbon fiber, said porous structural member containing a multiplicity of pores of dimensions greater than about 200 microns in diameter, said porous structural member further including carbon fill material within a portion of said pores such that the pores are essentially less than about 200 microns in diameter, said carbon fill material-containing porous structural member defining a composite carbon/carbon intermediate article which includes an outer surface; and,
a thin coating of diamond like carbon upon said outer surface of said composite carbon/carbon intermediate article, said composite article characterized as having a density gradient with a greatest density near the center of said composite article and a lower density near the surface of said composite article.

2. A composite article comprising:
a porous structural member formed of carbon fiber, said porous structural member containing a multiplicity of pores of dimensions greater than about 200 microns in diameter, said porous structural member further including carbon fill material within a portion of said pores such that the pores are essentially less than about 200 microns in diameter, said carbon fill material-containing porous structural member defining a composite carbon/carbon intermediate article which includes an outer surface; and,
a thin coating of diamond like carbon upon said outer surface of said composite carbon/carbon intermediate article, said composite article characterized as having a gradient density with a greatest density at one end of said composite article and a decreasing density towards the other end of said composite article.

3. A composite article comprising:
a head portion; and,
a stem portion including a unidirectional carbon fiber core surrounded by a braided carbon fiber sleeve including carbon fibers aligned at an angle from said unidirectional carbon fiber core so as to define a porous structural member containing a multiplicity of pores of preselected dimensions, said stem portion further including carbon fill material within a portion of said pores, said head portion attached to said stem portion at an end of said stem portion.

4. The composite article of claim 3 wherein a thin coating of diamond-like carbon is disposed upon outer surfaces of said composite article.

* * * * *